US012229984B2

(12) United States Patent
Krueger et al.

(10) Patent No.: US 12,229,984 B2
(45) Date of Patent: Feb. 18, 2025

(54) POSITIONING OF A PATIENT CARRIER (71) Applicant: KONINKLIJKE PHILIPS N.V., Eindhoven (NL)

(72) Inventors: Sascha Krueger, Hamburg (DE); Julien Senegas, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 708 days.

(21) Appl. No.: 17/289,926

(22) PCT Filed: Oct. 15, 2019

(86) PCT No.: PCT/EP2019/079881
§ 371 (c)(1),
(2) Date: Apr. 29, 2021

(87) PCT Pub. No.: WO2020/089417
PCT Pub. Date: May 7, 2020

(65) Prior Publication Data
US 2022/0005220 A1 Jan. 6, 2022

(30) Foreign Application Priority Data
Nov. 2, 2018 (EP) .................... 18204048

(51) Int. Cl.
*G06K 9/00* (2022.01)
*A61B 5/00* (2006.01)
(Continued)

(52) U.S. Cl.
CPC ................ *G06T 7/73* (2017.01); *A61B 5/055* (2013.01); *A61B 5/704* (2013.01); *A61B 6/0487* (2020.08);
(Continued)

(58) Field of Classification Search
None
See application file for complete search history.

(56) References Cited

U.S. PATENT DOCUMENTS

| 6,175,610 B1 | 1/2001 | Peter |
| 2013/0281818 A1 | 10/2013 | Vija et al. |

(Continued)

FOREIGN PATENT DOCUMENTS

| JP | 2018183525 A | * 11/2018 | ............. A61B 5/055 |
| WO | 2018069092 A2 | 4/2018 | |

(Continued)

OTHER PUBLICATIONS

Lea et al "3D Sensing Algorithms Towards Builiding an Intelligent Intensive Care Unit" AMIA Jt Summits Transl Sci Proc. 2013; 2013: p. 136-140.

(Continued)

*Primary Examiner* — Wei Wen Yang (57) ABSTRACT

A positioning control system for a patient carrier comprises a camera system to acquire image information from a detection range. An analysis module configured to access the acquired image information from the detection range and compute operator-activity within the detection range from the acquired image information. The operator-activity representing a spatio-temporal pattern of activities of an operator in the detection range. From the operator activity compute a location of a target anatomy that is selected to be imaged. The location of the target anatomy that is to be imaged can be derived from the spatio-temporal activity pattern of the operator during the preparation of the patient to be examined.

14 Claims, 4 Drawing Sheets

(51) Int. Cl.
*A61B 5/055* (2006.01)
*G06T 7/73* (2017.01)
*A61B 6/04* (2006.01)

(52) U.S. Cl.
CPC .............. *G06T 2207/10028* (2013.01); *G06T 2207/30004* (2013.01); *G06T 2207/30196* (2013.01)

(56) References Cited

U.S. PATENT DOCUMENTS

2013/0342350 A1   12/2013  Popescu
2018/0116518 A1    5/2018  Rinck et al.
2019/0008598 A1*  1/2019  Frimer ................... G16H 30/40

FOREIGN PATENT DOCUMENTS

WO         2018069479 A1    4/2018
WO    WO-2018217951 A1 *  11/2018  ......... A61B 1/00039

OTHER PUBLICATIONS

Lin et al "A Heat Map Based Algorithm for Recognizing Group Activities in Videos" IEEE Trans. Circuits and Systems for Video Technology, vol. 23, No. 11, pp. 1980-1992, 2013.
Search Report and Written Opinion from PCT/EP2019/079881 Mailed May 7, 2020.

\* cited by examiner

POSITIONING OF A PATIENT CARRIER

CROSS REFERENCE TO RELATED APPLICATIONS

This application is a U.S. national phase application of International Application No. PCT/EP2019/079881 filed on Oct. 31, 2019, which claims the benefit of EP application Ser. No. 18/204,048.5 filed on Nov. 2, 2018 and is incorporated herein by reference.

FIELD OF THE INVENTION

The invention pertains to a positioning control system for a patient carrier. Notably, the patient carrier is configured to support a patient to be examined in a diagnostic imaging system and to position the patient appropriately to acquire image data from a target anatomy that is to be examined. The positioning control system is configured to control the displacement of the patient carrier, for example from an outside-position where the patient to be examined is outside of the diagnostic imaging system to an inside-position where the patient to be examined, or at least the target anatomy is within the diagnostic imaging system where image data from the target anatomy can be acquired. In the outside-position usually the (final) preparation of a patient to be examined is done, while the actual acquisition of image data is done with the patient carrier with the patient to be examined in the inside-position.

BACKGROUND OF THE INVENTION

A medical imaging system with a range imaging-based control is known from the US patent application US2013/0281818.

The known medical imaging system comprises a scanner and a monitoring system including a range-imaging camera. The monitoring system is configured to capture spatial data of an object spaced away from the scanner. In particular the object is an operator and the spatial data relates to the operator's manual gestures. The monitoring system is able to control the medical imaging system based on the operator's gestures. These operator's gestures may be used to define an imaging area or to re-position a patient bed.

SUMMARY OF THE INVENTION

An object of the invention is to provide a positioning control system for a patient carrier that enables a more accurate and consistent positioning of the patient carrier relative to the diagnostic imaging system.

This object is achieved by the positioning control system of the invention comprising:
  a camera system having a detection range to acquire image information from the detection range and
  an analysis module configured to
    access the acquired image information from the detection range
    compute operator-activity within the detection range from the acquired image information,
    the operator-activity representing a spatio-temporal pattern of activities of an operator in the detection range, said activities associated with tactile manipulation of objects and
    from the operator activity compute a location of a target anatomy that is selected to be imaged.

The invention achieves to position the patient carrier relative to the diagnostic imaging system on the basis of monitoring of the operator's activities during preparation prior to the actual image acquisition. These operator's activities can be monitored and be evaluated for example for areas where the operator's activity level is highest or at least enhanced. An insight of the present invention is that the location of the target anatomy that is to be imaged can be derived from the spatio-temporal activity pattern of the operator during the preparation of the patient to be examined. The camera system acquires image information that represents motion in the camera's detection range. The more activities like motion of the operator's hands in specific areas during the preparation of the patient to be examined, the more likely that such areas correspond to the target anatomy to be imaged. For example, relatively intense motion of the operator's hands and arms correlate strongly with the positioning of a local receiver MR coil at the target anatomy. Also the spatial shape of the motion pattern may be indicative of the type and location of the planned scan (e.g. ECG and coil placement for cardiac scanning result in a quite unique pattern). For example, artificial intelligence, such as implemented as recursive neural networks (RNNs) could be used to derive the target anatomy to be imaged from a full exam preparation video stream. The tactile manipulations of the operator may relate to positioning and connecting of objects like auxiliary equipment such as a local radiofrequency (RF) transmit and/or receive antenna (array), monitoring equipment such as electro-encephalography or electro-cardiography equipment, notably application of electrodes on the patient's body. The tactile manipulations may also relate to the (preparation for) insertion of interventional instruments into the patient's body, such as biopsy needles, endoscopes and catheters or the placement of sterile drapes. Further, the tactile manipulations may be associated with position of elements for patient comfort such as head rests or knee rests to support the patient to be examined in its position for imaging. As there is a limited variety of actions, this may derived from a cumulative motion history (spatial activity map). The position of the target anatomy is computed from the spatio-temporal activity pattern of the operator. The relative positioning of the patient carrier to the imaging zone of the diagnostic imaging system can be detected or measured. Hence, on the basis of the computed location of the target anatomy relative to the patient carrier and the relative position of the patient carrier to the examination zone, the positioning control system can control the patient carrier to be displaced to its position where the target anatomy is in the imaging zone. Notably, good results are achieved by identifying zone of enhanced activities of the operator's tactile manipulations from the spatio-temporal activity pattern. In a zone of enhanced activity there is a higher level of activity of the operator, in that there is a higher rate of tactile movements, a higher number of repetition of movements, or higher amplitudes of tactile manipulations as compared to the average of the spatio-temporal pattern as a whole. Another example of a zone of enhanced activity is a zone of maximal level of operator activities. There is no need for cumbersome auxiliary equipment such as light visor laser devices. Also the positioning is not hampered by the patient's body being (partly) obstructed being covered by blankets or by the local receiver coil placed on or near the patient's body.

The diagnostic imaging system may be a magnetic resonance examination system, a computed tomography system, an x-ray examination system or a nuclear medicine tomography system. For each of these examination or imaging modalities, the operator during preparation will pay more attention to the region to be imaged or perform very specific actions indicative of the region to be imaged. That is, the target anatomy to be imaged may be derived from enhanced activity in the spatio-temporal activity pattern, or from the recognition of specific activity patterns that are indicative from the target anatomy to be imaged. For MRI, receiving RF coils may be placed that the region to be imaged, in other modalities other (auxiliary) equipment may be placed in relation to that region of interest, and in any case the operator will pay more attention to the region of interest to make sure the patients target area is properly seated to ensure rest during the examination or imaging procedure. In interventional procedures, the relation between an area of higher operator activity may be more remote from the region of interest. For example, preparation of arterial access in the patient's groin will indicate a cardiac examination if the operator's hand motions are indicative of a longer catheter or a liver or kidney intervention is more likely if the hand motions are indicative of a shorter device. On the other hand, preparation of arterial access in the patient's neck may be indicative for a stroke intervention where the patient's brain in the region-of-interest.

In brief, the positioning control system for a patient carrier comprises a camera system to acquire image information from a detection range. An analysis module configured to access the acquired image information from the detection range and compute operator-activity within the detection range from the acquired image information. The operator-activity representing a spatio-temporal pattern of activities of an operator in the detection range. From the operator activity compute a location of a target anatomy that is selected to be imaged. The location of the target anatomy that is to be imaged can be derived from the spatio-temporal activity pattern of the operator during the preparation of the patient to be examined.

These and other aspects of the invention will be further elaborated with reference to. the embodiments described herein.

In an implementation of the positioning control system of the invention, an OA-filter is employed to filter out the operator activity from the dynamic image information that may contain motion-information relating to movement of the operator and other motion, such as (in)voluntary motion of the patient. The OA-filter distinguishes between motion made by the operator from other motion that occurs in the detection range. The OA-filter may utilise detected motion of an upright standing person that is hence recognised as the operator. The patient to be examined, to the contrary during preparation is more likely to lie horizontally on the patient support. The OA-filter may be implemented in image processing as a pattern recognition which distinguishes motion by the operator from other spurious motion. For example, motion at a level below a pre-set threshold may be discarded by the OA-filter as e.g. breathing or slight patient movement for comfort. The OA-filter may also be implemented in artificial intelligence by way of a trained network that is trained to discriminate between operator's activities that are representative for imaging of specific anatomies.

In a further implementation of the positioning control system of the invention, an EA-filter is employed to distinguish motion relating to the examination being planned from other motion in or near the region-of-interest. Thus the EA-filter is configured to filter-out motion related to examination activities from other motion events For example, the EA -filter may filter for areas of more intense motion from a lower level of motion by the operator that is not specific for examination of the target anatomy as issue. The EA-filter may also filter-out image information of the operator's movements that are not specific for the target anatomy at issue. For example, auxiliary equipment recognised at the patient's feet end, may be filtered out when the region-of-interest is already determined as at the patient's upper body part. The EA-filter may also block motion that is attributed to pre-determined motion pattern, such as originating form a predetermined tremor of the patient to be examined. Main body parts, e.g. head, torso, arms and legs, may be recognised by the EA-filter and motion in any of the body parts and not relating to the region-of-interest may be filtered-out by the EA-filter.

In a further embodiment motion patterns or segments thereof which are descriptive of an examination type and location are learned by a neural network.

In yet another embodiment of the invention, the camera system is a 3D camera which acquires volumetrically resolved image information. This allows to capture operator activities, such as motion of arms and hands resolved in three spatial directions (in the framework of the body of the patient to be examined: left-right, feet-head and anterior posterior).

In another implementation of the invention, the filtering for operator activities in the acquired image information makes use of information of the position on the patient carrier of the body of the patient to be examined. This achieves to distinguish motion of the operator from motion of the patient. Motion of the patient can be distinguished on the basis of a field-of-view restriction to the region of the patient support's top surface and some margin around it.

The invention further pertains to a diagnostic imaging system, notably an magnetic resonance examination system, having an imaging zone and comprising a patient carrier positioning control system and a positioning control system of the invention as disclosed above wherein the analysis module is configured to compute the patient carrier's spatial position which places the target anatomy in the imaging zone.

The diagnostic imaging system of the invention is able to properly position the patient carrier so that the region-of-interest is in the imaging zone. Because the region-of-interest is found from the spatio-temporal activity pattern of the operator when preparing the patient to be examined for the examination, cumbersome systems such as a laser light visor can be dispensed with. Moreover, the diagnostic imaging system of the invention is able to accurately determine the location of region-of-interest even when that is covered by blankets, sterile drapes and the like.

The invention also pertains to a method of positioning a patient carrier with respect to a diagnostic imaging system, the method comprising to monitor an operator's activities areas of higher level where the operator's activity level is highest and derive the location of the target anatomy that is to be imaged from the spatio-temporal activity pattern of the operator.

The method of the invention achieves to locate the region-of-interest accurately. There is no need for a cumbersome light visor and the region-of-interest may be well located even if not directly visible.

The invention also relates to a computer program as defined in the claims. The computer program when installed in a positioning control system for the patient carrier of a diagnostic imaging system, achieves to locate the region-of-interest accurately. There is no need for a cumbersome light visor and the region-of-interest may be well located even if not directly visible. The computer program of the invention can be provided on a data carrier such as a CD-ROM disk or a USB memory stick, or the computer program of the invention can be downloaded from a data network such as the world-wide web such as from The Cloud.

These and other aspects of the invention will be elucidated with reference to the embodiments described hereinafter and with reference to the accompanying drawing wherein

DETAILED DESCRIPTION OF THE EMBODIMENTS

Figure 1:
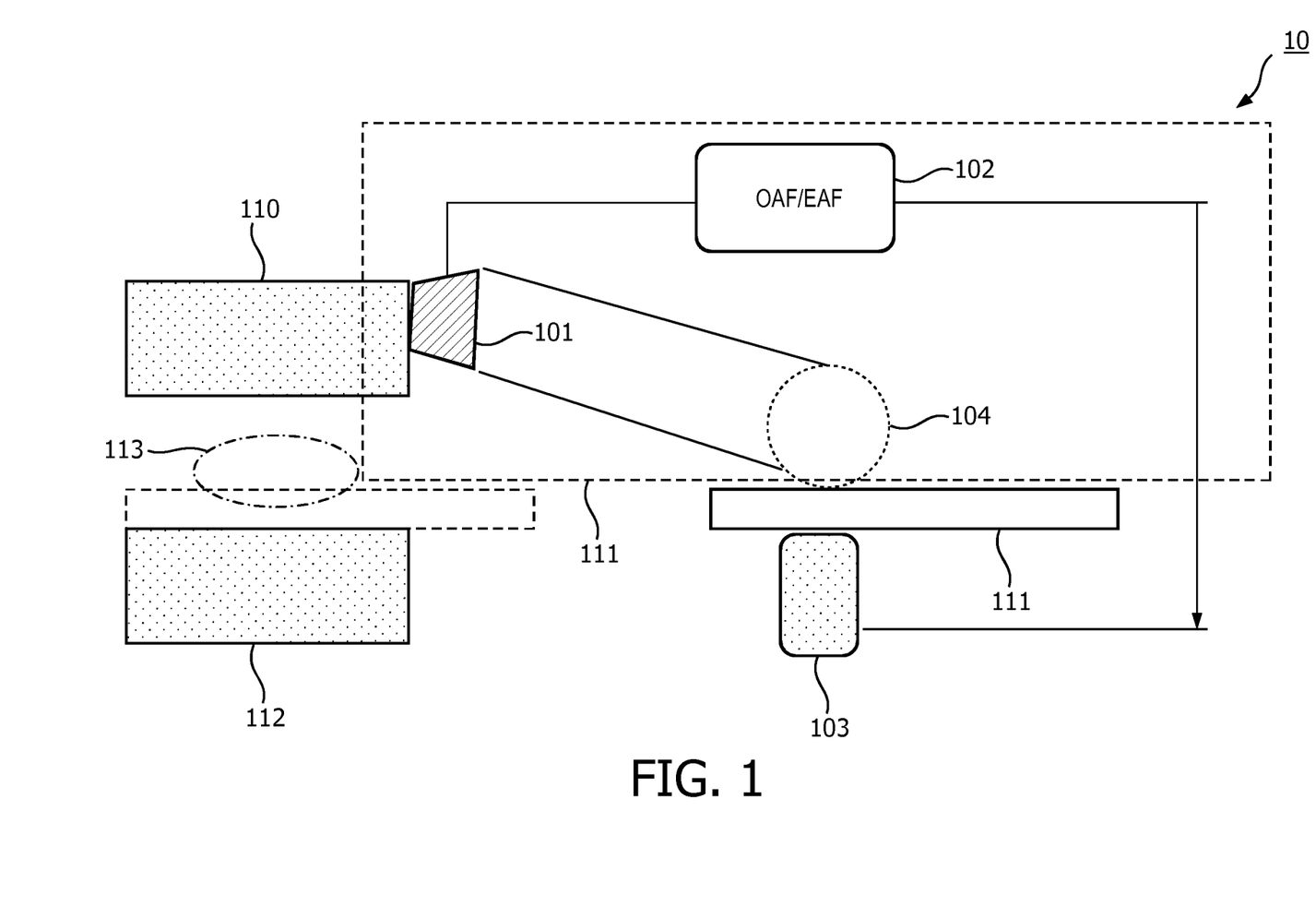
FIG. 1 shows a diagrammatic representation of a diagnostic imaging system provided with a positioning control system according to the invention.

FIG. 1 shows a diagrammatic representation of a diagnostic imaging system 110 provided with a positioning control system 10 according to the invention. The positioning control system 10 includes a camera system 101 that may be mounted to the structure of the diagnostic imaging system 110. For example the diagnostic imaging system may be a magnetic resonance examination system and the camera system 101 may be mounted to e.g. to the ceiling of the room in which the magnetic resonance examination system is located or to the gantry or the outside covers of the magnetic resonance examination system's 110 main magnet. The camera system has a detection range 104 from which the camera system can pick-up image information. The diagnostic imaging system comprises a patient carrier that is moveable from a position outside the examination zone 113. The patient to be examined may be positioned on the patient carrier and moved in to the examination zone 113, such that image data may be acquired from a region-of-interest of the anatomy of the patient to be examined. When image data are acquired the patient to be examined is positioned such that the region-of-interest is in an imaging zone 112 from which data with high image quality can be acquired. For example for a magnetic resonance examination system the imaging zone 112 corresponds to a volume where there is very good spatial homogeneity of the main magnetic field and very good linearity of the gradient encoding magnetic fields. For a computed-tomography (CT) system the imaging zone 112 corresponds to a volume from which irradiation with x-radiation is done from a wide range of orientations that span at least $\pi$ radians minus the angular span of the CT systems' detector array.

During preparation to the patient to be examined for the imaging procedure, the patient is placed on the patient support 111 while that is positioned such that the patient to be examined is still outside of the diagnostic imaging system (i.e. outside the bore of a MRI-system or a CT-system). The radiology staff will stand next to the table 111 engaged in various activities such as placing RF receiver coils on the patient's body and arranging that the patient's body is most properly seated on the patient support, preparing the patient for access of an instrument, applying ECG electrodes and so on. All these preparations will involve higher intensity of movement of the operators hands at the patient to be examined, e.g. at the region-of-interest or at an area at a pre-determined position relative to the region-of-interest.

The camera system 101 has a detection range 104 at the patient support when outside of the diagnostic imaging system. When the camera system is formed by a 3D camera, the detection range 104 is a volume and the 3D camera may spatially resolve that detecting range in a volumetric manner. When the operator is active, the operator's movements, notably of the operator's arms and hands are dynamically imaged by the camera system 101. The acquired image data are applied form the camera unit to the analysis module 102 which derives the spatio-temporal pattern of the operator's activities in the detection range 104. From that spatio-temporal pattern, the analysis module 102, by way of the OA-filter (OAF) and the enhanced activity filter (EAF), derives the location of the target anatomy, i.e. the region-of-interest, to be imaged. The information on the location of the region-of-interest is fed from the analysis module to a drive unit 103 for the patient support. The drive unit 103 functions the displace the patient support 111 so that the identified region-of-interest is accurately positioned in the imaging zone 112 of the diagnostic imaging system. Thus, from the spatio-temporal motion pattern of the operator's hands by the camera system, the analysis system filters image information that is pertinent of the region-of-interest or the target anatomy. In this way the location of the region-of-interest is derived from the operator's activity as monitored by the camera system. On the basis of the location of the region-of-interest the patient support is driven into the diagnostic imaging system to position the region-of-interest at the imaging zone 112. This is achieved in that the information on the location of the region-of-interest is employed to control a motor of the drive unit which displaced the patient support carrying the patient to be examined.

The OA-filter is configured to distinguish motion of the operator from other movements in the detection range 104. The OA-filter may make use of the insight that the operator is usually standing upright while the patient to be examined lies down on the patient support. In a more sophisticated implementation the OA-filter may contain artificial intelligence that is able to distinguish particular spatio-temporal activity patterns and assign them to activities of the operator and relate to a particular region-of-interest.

The EA-filter is configured to distinguish motions that pertain to the planned examination from other motion in the detection range. E.g. pre-determined patterns of a patient's tremor or free breathing motion may be separated by the EA-filter from the operator's movement that relate the region-of-interest, e.g. placement of RF receiver coils at the region-of-interest. In a more sophisticated implementation the EA-filter may contain artificial intelligence that is able to distinguish particular spatio-temporal activity patterns and assign them to activities of the operator and relate to a particular region-of-interest.

Figure 2:
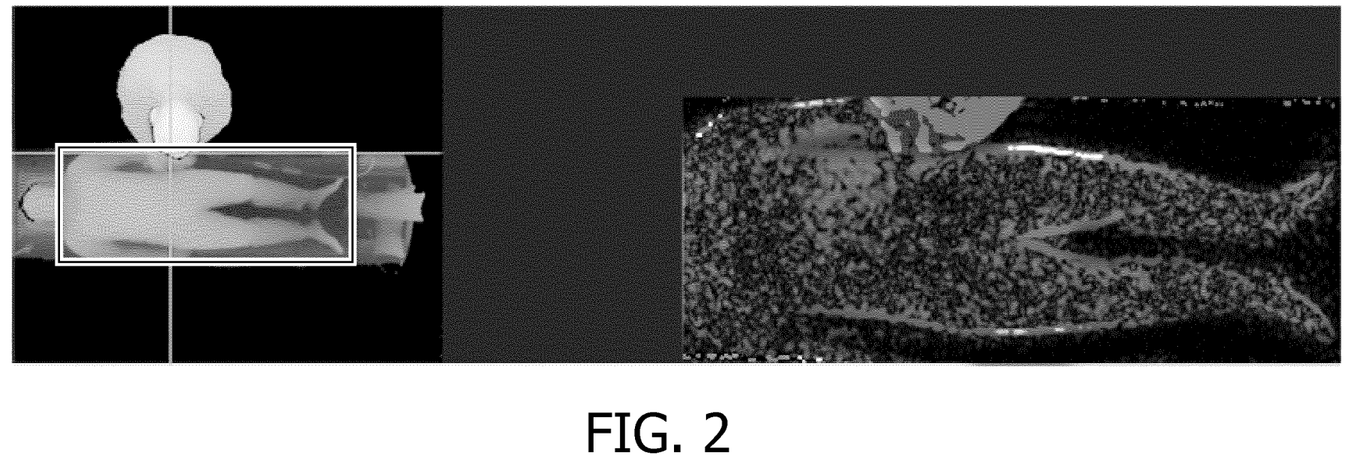
FIG. 2 shows an example of a spatio-temporal activity pattern of the preparation of magnetic resonance imaging of the patient's left hand.

FIG. 2 shows an example of a spatio-temporal activity pattern of the preparation of magnetic resonance imaging of the patient's left hand. The left part of the figures shows a still picture of the operator standing next to the patient to be examined. The right part of the figure shows the activity pattern of the operator's hand traced as time progresses. Clearly, the spatio-temporal activity pattern shows enhanced activity at the patient's left hand. Hence, the analysis module will derive that the patient left hand is the highly likely region-of-interest.

Figure 3:
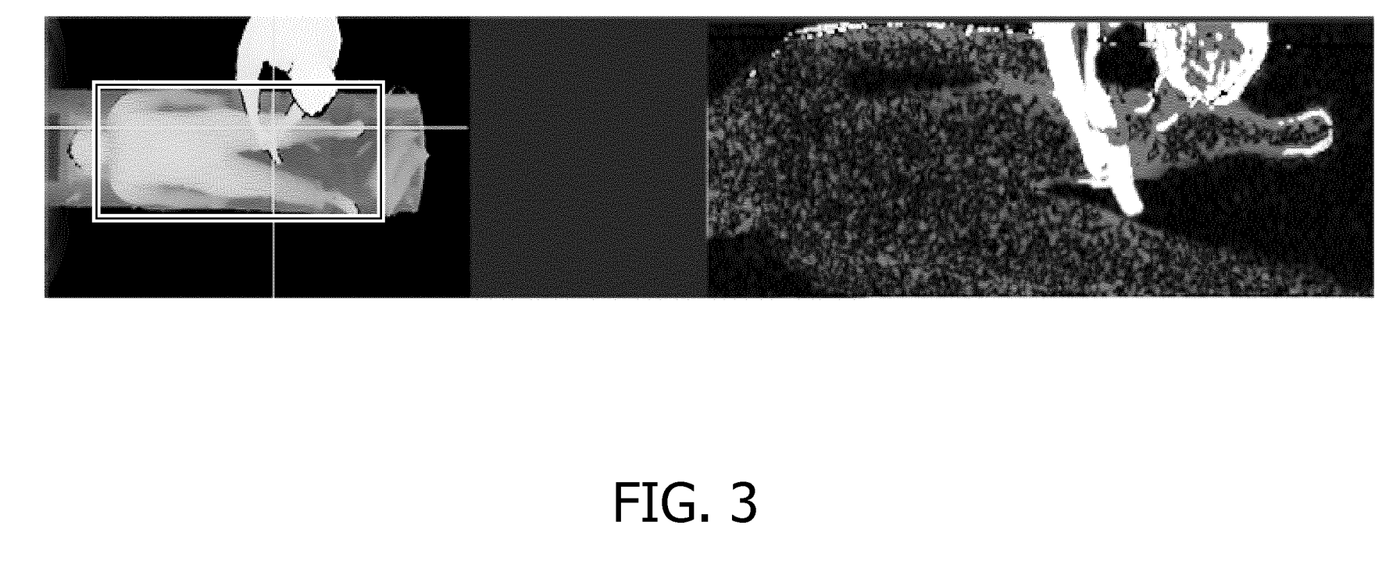
FIG. 3 shows an example of a spatio-temporal activity pattern of the preparation of magnetic resonance imaging of the patient's left knee and FIGS. 4 and 5 show to distinguish between operator activities for preparing the patient to be examined for an abdominal examination of a for a head examination, respectively.

FIG. 3 shows an example of a spatio-temporal activity pattern of the preparation of magnetic resonance imaging of the patient's left knee. The left part of the figures shows a still picture of the operator standing next to the patient to be examined. The right part of the figure shows the activity pattern of the operator's hand traced as time progresses. Clearly, the spatio-temporal activity pattern shows enhanced activity at the patient's left knee. Hence, the analysis module will derive that the patient left knee is the highly likely region-of-interest.

Figure 4:
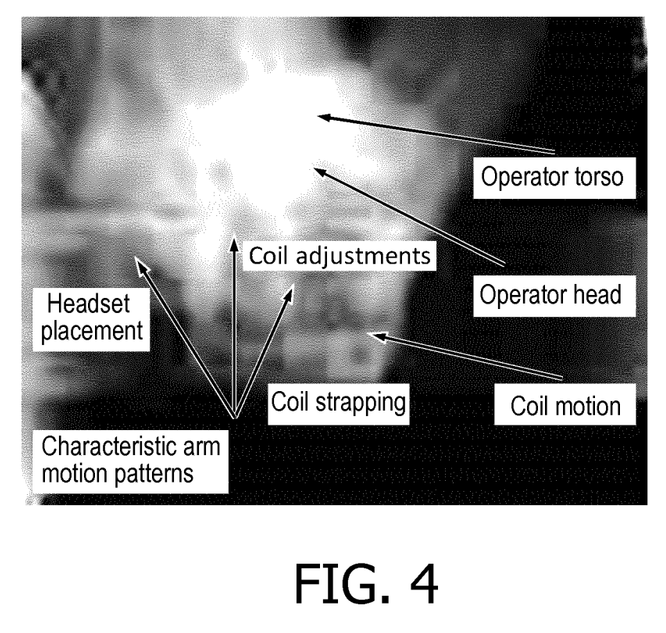
Figure 5:
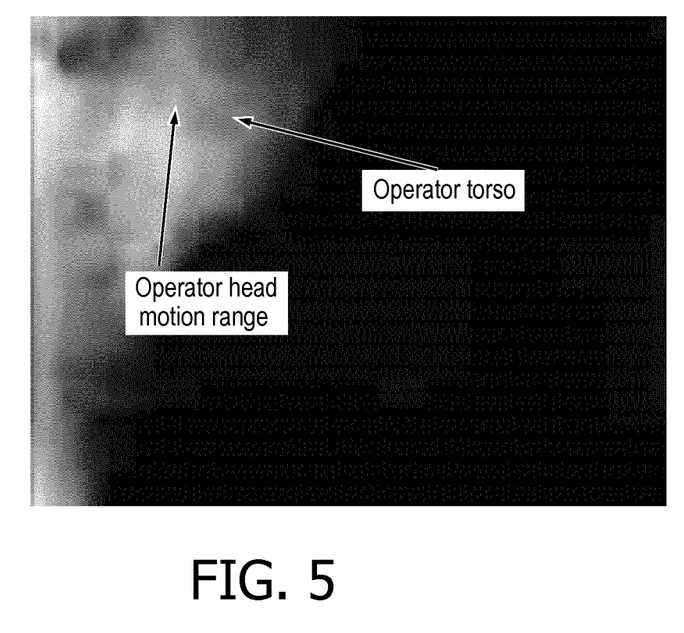

FIGS. 4 and 5 show to distinguish between operator activities for preparing the patient to be examined for an abdominal examination of a for a head examination, respectively. FIG. 4 shows an accurate spatio-temporal motion pattern for an abdominal examination. Notably FIG. 4 shows that operator being predominantly occupied with placing an anterior coil on the patient's torso. Some secondary activity near the patient's head is attributed to placing the audio headset. FIG. 5 shows an accumulated spatio-temporal motion pattern for a head examination. FIG. 5 shows motion patterns near the patient's head not only from positioning the audio-headset, but also to closing the head coil and securing correct fit of the head coil on both sides of the patient's head. This activity pattern leads to a characteristic high lateral and low head-feet head motion range. Lower overall intensity is indicative of an examination with fast setup workflow which appears to be typical for a head examination. FIGS. 4 and 5 show that motion patterns for an abdominal examination or a head examination, respectively differ. Thus, from the recognising of the motion pattern, the invention is able to derive during the preparation phase what part of the patient's anatomy to be imaged.

The invention claimed is:

1. A positioning control system for a patient carrier of a diagnostic imaging system, the positioning control system comprising:
    a camera system having a detection range, wherein the camera system is configured to acquire image information from the detection range; and
    an analysis module configured to:
        access the acquired image information from the detection range;
        compute operator-activity within the detection range from the acquired image information, the operator-activity representing a spatio-temporal pattern of motions of hands and arms of an operator in the detection range associated with tactile manipulation of objects by the operator within the detection range; and
        from the operator-activity, compute a location of a target anatomy of a patient on the patient carrier that is selected to be imaged by the diagnostic imaging system.
2. The positioning control system of claim 1, wherein the analysis module includes an OA-filter to filter the operator-activity from the acquired image information.
3. The positioning control system of claim 1, wherein the analysis module includes an EA-filter to filter image information indicating enhanced activity's spatial distribution from the acquired image information.
4. The positioning control system of claim 1, wherein the camera system is a 3D camera system that is enabled to acquire volumetrically resolved image information from the detection range.
5. The positioning control system of claim 1, wherein the analysis module is further configured to:
    detect a region of a body of a patient to be examined positioned on the patient carrier from the acquired image information; and
    filter-out operator-activity of the operator from the acquired image information using the detected region of body of the patient.
6. A diagnostic imaging system including an imaging zone, the diagnostic imaging system comprising:
    a patient carrier positioning control system for positioning a patient carrier;
    a camera system having a detection range, wherein the camera system is configured to acquire image information from the detection range; and
    an analysis module configured to:
        access the acquired image information from the detection range;
        compute operator-activity within the detection range from the acquired image information, the operator-activity representing a spatio-temporal pattern of motions of hands and arms of an operator in the detection range associated with tactile manipulation of objects by the operator within the detection range;
        from the operator-activity, compute a location of a target anatomy of a patient on the patient carrier that is selected for diagnostic imaging by the diagnostic imaging system; and
        compute a spatial position of the patient carrier that places the target anatomy of the patient in the imaging zone for the diagnostic imaging by identifying a zone of enhanced activities of the tactile manipulation of the objects from the spatio-temporal pattern of activities.
7. The diagnostic imaging system of claim 6, wherein the analysis module includes an OA-filter to filter the operator-activity from the acquired image information.
8. The diagnostic imaging system of claim 6, wherein the analysis module includes an EA-filter to filter image information indicating enhanced activity's spatial distribution from the acquired image information.
9. The diagnostic imaging system of claim 6, wherein the camera system is a 3D camera system that is enabled to acquire volumetrically resolved image information from the detection range.
10. The diagnostic imaging system of claim 6, wherein the analysis module is further configured to:
    detect a region of a body of a patient to be examined positioned on the patient carrier from the acquired image information; and
    filter-out operator-activity of the operator from the acquired image information using the detected region of the body of the patient.
11. The positioning control system of claim 1, wherein the analysis module is further configured to drive the patient carrier into the diagnostic imaging system to position the target anatomy in an imaging zone of the diagnostic imaging system for performing diagnostic imaging of the target anatomy.
12. The positioning control system of claim 2, wherein filtering-out the operator-activity from the acquired image information comprises discarding motion at a level below a pre-set threshold.

13. The diagnostic imaging system of claim 6, wherein the analysis module is further configured to drive the patient carrier into the computed spatial position of the patient carrier placing the target anatomy of the patient in the imaging zone for the diagnostic imaging.

14. The diagnostic imaging system of claim 7, wherein filtering-out the operator-activity from the acquired image information comprises discarding motion at a level below a pre-set threshold.

* * * * *